United States Patent [19]
Hurlburt et al.

[11] Patent Number: 5,631,390
[45] Date of Patent: May 20, 1997

[54] HALOGENATION OF COBALT DICARBOLLIDE

[75] Inventors: Paul K. Hurlburt; Kent D. Abney; Scott A. Kinkead, all of Los Alamos, N.M.

[73] Assignee: The Regents of the University of California, Alameda, Calif.

[21] Appl. No.: 455,372

[22] Filed: May 31, 1995

[51] Int. Cl.$^6$ ............................... C07F 5/02; C07F 15/06
[52] U.S. Cl. ................................ 556/7; 556/140; 568/4
[58] Field of Search ........................... 556/7, 140; 568/4

[56] References Cited

PUBLICATIONS

"New Weakly Coordinating Anions," *Inorg. Chem.* 1993, 32, 1982–1990.
"Dicarbollyl Derivatives of the Transition Metals. Metallocene Analogs," *Journal of the American Chemical Society,* 90:4, Feb. 14, 1968.
"B–Halogen Derivatives of the BIS(1,2–Dicarbollyl)Cobalt(III) Anion," *Polyhedron,* vol. I, No. 6, pp. 511–519, 1982.
LA–11695, "Cobalt(III) Dicarbollide: A Potential $^{137}$Cs and $^{90}$Sr Waste Extraction Agent," Los Alamos National Laboratory, Feb. 1990.
Selucky, P; Base, K.; Plesek, J.; Hermanek. S.;Rais, J.; Czechoslovakian Patent No. 215282, 1985, and attached copy of English language abstract.
"Effects of amine–borane structure on the stoichiometry, rate and mechanism of raction with hypochlorous acid: hydride oxidation versus B–chlorination," *Inorganica Chimica Acta,* 211, (1993), pp. 187–194.
"Fission Product Separation Using Ion Exchange, Solvent Extraction and Cobalt Dicarbollide," LAUR–94–3647, Los Alamos National Laboratory, Oct. 28, 1994.
"The Synthesis, Characterization and Structure of Chlorinated Derivatives of the Cobalt Dicarbollide Anion," Abstract, American Chemical Society 207th ACS National meeting, San Diego, CA, Mar. 13–17, 1994.
"The Preparation and Characterization of the (3)–1,2– and (3)–1,7– Dicarbadodecahydroundecaborate(–1) Ions", *Journal of the American Chemical Society,* 90:4, Feb. 14, 1968.
"The Reconstruction of the 1,2–Dicarbaclovododecaborane(12) Structure by Boron–Atom Insertion with (3)–1, 2–Dicarbollide Ions," *Journal of the American Chemical Society,* 90:4, Feb. 14, 1968.
"The Polyhedral $B_9C_2H_{11}$, $B_8C_2H_{10}$, $B_7C_2H_9$, and $B_6C_2H_9$, and $B_6C_2H_8$ Carboranes and the $B_7C_2H_{13}$ System," *Journal of the American Chemical Society,* 90:4, Feb. 14, 1968.

*Primary Examiner*—Porfirio Nazario-Gonzalez
*Attorney, Agent, or Firm*—Samuel M. Freund; Richard J. Cordovano

[57] ABSTRACT

A method for selectively adding chlorine, bromine, or iodine to cobalt dicarbollide anions by means of electrophilic substitution reactions. Halogens are added only to the B10 and B10' positions of the anion. The process involves use of hypohalous acid or N-halosuccinimide or gaseous chlorine in the presence of iron.

10 Claims, 1 Drawing Sheet

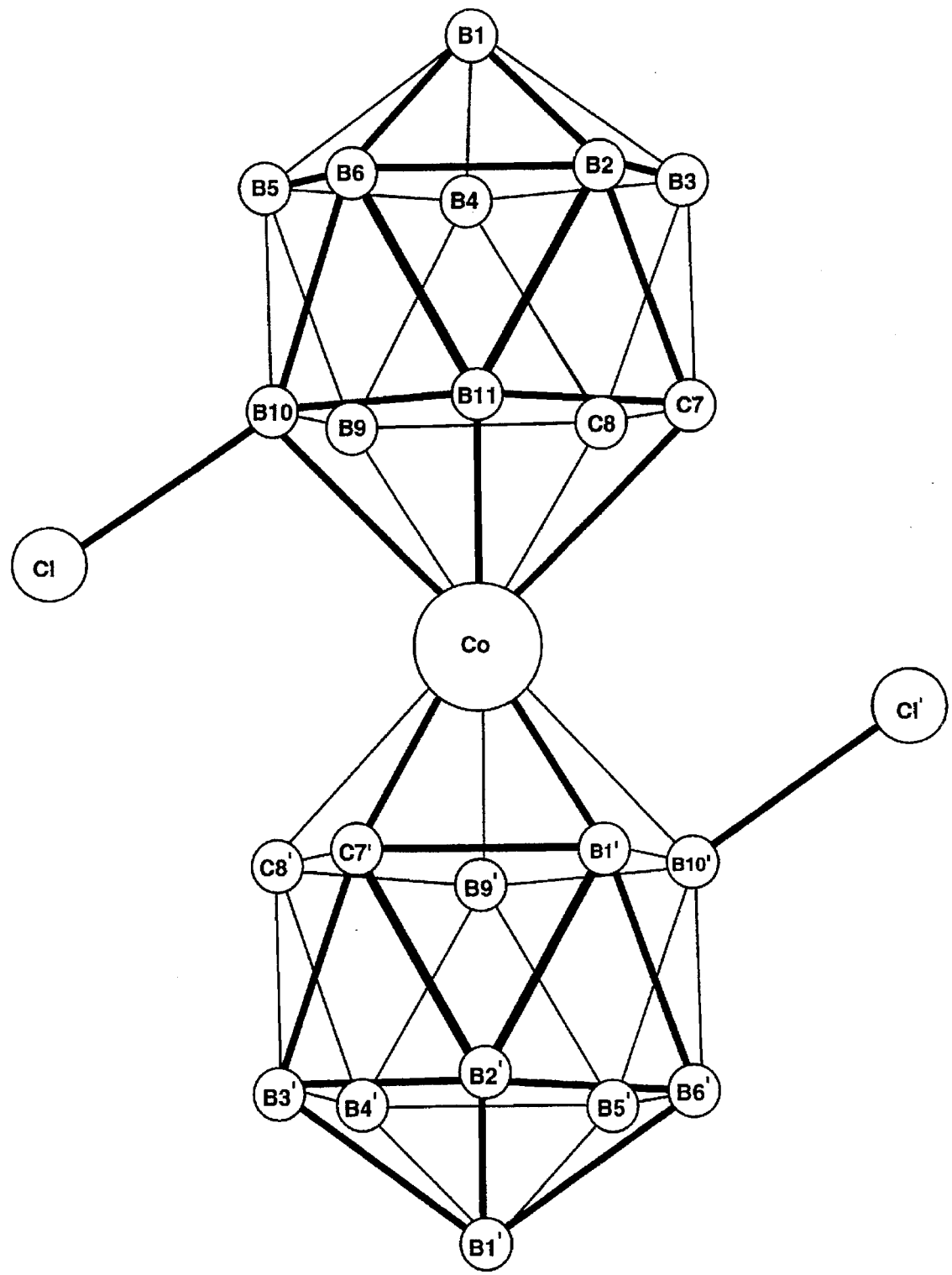

HALOGENATION OF COBALT DICARBOLLIDE

BACKGROUND OF THE INVENTION

This invention relates to the field of materials science and, more particularly, to nonmetallic materials and powder metallurgy. This invention was made with government support under Contract No. W-7405-ENG-36 awarded by the U.S. Department of Energy. The government has certain rights in the invention.

The cobalt dicarbollide anion, $[Co(7,8-C_2B_9H_{11})_2]-$, is of interest to researchers because it is extremely robust, in that it is capable of withstanding strong acids, moderate bases, high temperatures, and intense radiation. Due to these properties, cobalt dicarbollide is being investigated for use in a number of applications. It may be useful in boron neutron capture therapy, where it is used as a carrier of boron-10. A cobalt dicarbollide salt may be administered to a living subject in such a manner that it concentrates near a malignant growth. Upon neutron irradiation, $^{10}B$ nuclei absorb neutrons and release alpha particles, which damage or destroy the tumor.

Cobalt dicarbollide may be useful as a tumor imaging reagent. Its kinetic stability and resistance to radiolytic degradation make it unlikely that radioactive cobalt would be released in a subject to which it is administered in order to image, by means of emitted radiation, a portion of the subject's body.

Cobalt dicarbollide is being investigated as a weakly coordinating counter-ion for certain polymerization catalysts, where turnover rates are dependent on vacant sites on the metal center or the degree of dissociation of the anion. Examples of such catalysts are $[Cp_2ZrCH_3]+$ and $[Cp_2ThCH_3]+$, where Cp is cyclopentadiene anion. The large size-to-charge ratio of cobalt dicarbollide aids in the coordinative unsaturation of the Zr or Th center.

Radioactive cesium and strontium are components of high-level nuclear waste which cause a great deal of concern in regard to safe storage of the waste, since storage is the only currently feasible disposal method. The intense radiation and thermal energy emitted by high-level nuclear waste pose significant problems in design of waste containers and storage facilities. Waste storage capacity at nuclear power plants is limited. Also, Cs and Sr are present in low-level nuclear waste generated in nuclear power plants. Removal of cesium and strontium from the waste will make handling and storage much safer and easier and reduce the volume of the waste. This may be accomplished by using cobalt dicarbollide in processing the waste. Cesium-137 and $^9Sr$ are also used in commercial applications such as sterilization of medical equipment, treatment of sewage, and thermoelectric generators; recovery and re-use of these elements is desirable. Cobalt dicarbollide is capable of extracting cesium and strontium (under different conditions from those used for cesium) from acidic aqueous solutions into an organic solvent.

Although cobalt dicarbollide is quite stable, the chlorinated and brominated derivatives exhibit even greater stability to degradation by acidic media and intense radiation. Protection at the B10 and B10' positions is necessary for increased stability of cobalt dicarbollide in 3M $HNO_3$. When the number 10 positions are protected with halogens, use of the halogenated derivatives provides the same separation efficiency as unhalogenated cobalt dicarbollide. Thus, it is desirable to use these derivatives in extraction processes. Use of dihalogenated cobalt dicarbollide will result in less halogenated waste than use of more highly substituted compounds and it is less costly, since less halogenation reagent is required to make it. Previous preparations of chlorinated cobalt dicarbollide have used $Cl_2$ with gamma or ultraviolet radiation or $KClO_3$ in aqueous HCl. These yield up to six different products, with up to seven chlorine atoms per anion, which are then separated chromatographically, using harsh conditions or expensive reagents. Reported preparations of the brominated derivatives of the cobalt dicarbollide anion have yielded either the hexa-bromo derivative or a mixture of products.

SUMMARY OF THE INVENTION

This invention is a method for selectively adding chlorine, bromine, or iodine to cobalt dicarbollide anions by means of electrophilic substitution reactions. Halogens are added only to the B10 and B10' positions of the anion. The process involves use of hypohalous acid or N-halosuccinimide or gaseous chlorine in the presence of iron.

In a broad embodiment, the invention is a process for halogenating cobalt dicarbollide anions in which a halogen atom is added only to a boron atom located in the number 10 position of each cage of a cobalt dicarbollide anion or substituted cobalt dicarbollide anion, said process comprising:

a. reacting cobalt dicarbollide anions with a halogenation agent selected from a group consisting of an N-halosuccinimide, hypohalous acid, and iron and gaseous chlorine, where the halogen of said hypohalous acid or N-halosuccinimide is chosen from a group consisting of chlorine, bromine, and iodine, and where said reaction is conducted by a method chosen from a group consisting of:
(1) forming a mixture comprised of tetraalkylammonium cobalt dicarbollide, hypohalous acid, and water, and agitating said mixture for a time period sufficient for halogenation to take place, where the pH of said mixture is less than about 6.0;
(2) forming a mixture comprised of finely divided iron, a polar organic solvent, and x cobalt dicarbollide, and adding chlorine gas to said mixture for a period of time sufficient for chlorination to take place, where the number of moles of iron in said mixture is equal to at least half the number of moles of x cobalt dicarbollide and where x is a cation chosen from a group consisting of hydrogen, lithium, sodium, potassium, rubidium, cesium, trialkylammonium, and tetraalkylammonium; and
(3) forming a solution of x cobalt dicarbollide or a substituted x cobalt dicarbollide and an N-halosuccinimide in a polar organic solvent and agitating the solution for a time period sufficient for halogenation to take place; where x is a cation chosen from a group consisting of hydrogen, lithium, sodium, potassium, rubidium, cesium, trialkylammonium, and tetraalkylammonium, and where said substituted x cobalt dicarbollide has a substituent group attached to one or more of the carbon and boron atoms of the cobalt dicarbollide anion cages by means of a linking atom chosen from a group consisting of carbon, oxygen, nitrogen, phosphorus, and sulfur; and b. recovering from said mixture or solution a solid material comprised of cobalt dihalo dicarbollide or a substituted cobalt dihalo dicarbollide.

BRIEF DESCRIPTION OF THE DRAWING

The Drawing depicts the structure of a chlorinated cobalt dicarbollide anion. Atoms are labeled with chemical symbols and a number indicating their position in the anion. Twenty hydrogen atoms, one attached to each boron atom and carbon atom excepting the boron atoms to which chlorine atoms are attached, are not shown. The structure consists of two polyhedrons or cages, each having 20 sides and 12 vertices, linked by a single cobalt atom at a vertex of each polyhedron.

DETAILED DESCRIPTION OF THE INVENTION

The term "dicarbollide" was adopted by those skilled in the art because the chemical nomenclature system provides a name which is too cumbersome for convenient use in written and verbal communication. The commonly used names are used herein.

The reactions of this invention are electrophilic substitution reactions in which one of three reaction systems are used. The dicarbollide starting materials which are used are cobalt dicarbollide compounds where the cation is hydrogen, lithium, sodium, potassium, rubidium, cesium, trialkylammonium, or tetraalkylammonium. Cobalt dicarbollide anions which have alkyl groups or other substituent groups attached to one or more of the cage carbon and/or boron atoms in place of hydrogen atoms may be halogenated by practice of this invention.

In one reaction system, hypochlorous, hypobromous, or hypoiodous acid is used to provide the halogen atoms. In experimentation regarding this invention, hypochlorous acid, which is unstable, was prepared by addition of aqueous NaOCl to 6M HCl. This reaction system can be used only when tetraalkylammonium cobalt dicarbollide is the starting material, but the cation may easily be replaced with another after halogenation. Compounds other than those of this invention resulted upon use of the trimethyl ammonium and cesium salts as starting materials. Chlorination of tetramethylammonium cobalt dicarbollide by hypochlorous acid is unique in that the reaction gives exclusively B10, B10' disubstitution and does not proceed to further substitution at room temperature. It is believed that the same is true for bromination and iodination.

In a second reaction system, cobalt dicarbollide compounds with the cations mentioned above are used in chlorination by means of chlorine gas in the presence of iron. This reaction stops at dichlorination; if iron is not present, the reaction continues to addition of chlorine atoms at positions in addition to the number 10 position of each cage.

In a third reaction system, cobalt dicarbollide compounds of the cations mentioned above are used in halogenation by means of N-chlorosuccinimide, N-bromosuccinimide, or N-iodosuccinimide. These reactions are sufficiently gentle that halogenation in the number 10 position of each cage will take place without destroying the substituent groups of a substituted cobalt dicarbollide, that is, a cobalt dicarbollide anion having a substituent group attached to one or more of the cage carbon and boron atoms.

Following are examples of work done in regard to the present invention, followed by additional information on the reaction system used in each example.

EXAMPLE 1

Tetramethyl ammonium cobalt dicarbollide, $[(CH_3)_4N]$ $[Co(7,8-C_2B_9H_{11})_2]$, in the amount of 0.57 g (1.43 mmol) was dissolved in 120 ml of a mixture of 50 vol % tetrahydrofuran (THF) and 50 vol % isopropanol at room temperature. Iron filings (0.40 g, 0.72 mmol) were added to the resulting orange solution. Chlorine gas was sparged through the solution for two hours. The yellow solution obtained upon chlorine addition was evaporated to dryness and the resulting dark yellow solid was washed with two 50 ml portions of water to remove iron chloride. The solid was then dissolved/mixed in THF/isopropanol and the liquid was filtered to remove solid material, such as iron. Tetramethylammonium cobalt dichloro dicarbollide (0.61 g) was recovered by evaporating the solution to dryness, for a yield of 91%.

It is expected that almost any polar organic solvent may be used. However, it is desirable to limit the choice of solvents to those which are not chlorinated by the chlorine gas, thus avoiding generation of chlorinated waste and excessive use of chlorine. In the experimentation, isopropanol was mixed with THF because THF is expensive. It is believed likely that use of more than 50% isopropanol with THF would have resulted in chlorination of the isopropanol. Also, THF is easily chlorinated. It is expected that ferric chloride could be used instead of iron, as the mechanism of the reaction involves chlorination of the iron and formation of electrophilic chlorine. The amount of iron present in the reaction mixture should be at least half the amount of cobalt dicarbollide, where both amounts are expressed in moles. This is necessary to avoid the presence of free chlorine radicals in the reaction solution; the presence of such radicals would result in addition of more than two Cl atoms to each cobalt dicarbollide molecule. Use of more than this amount of iron will not improve the synthesis. Use of iron is an important feature of the invention, as it "stops" the reaction at dihalogenation. Without iron, more than one Cl atom would be added to each cage. Chlorine should be bubbled into the solution at a rate which is sufficiently low that the temperature of the solution is not raised by the heat of reaction to a point where excessive chlorination of the solvent takes place. Of course, this temperature varies, depending on the solvent selected, and a higher solution temperature speeds up the reaction. When bubbling chlorine gas into a solution containing finely divided iron, an excess of Cl is required. If the solution were to be extremely well agitated, it is expected that the stoichiometric amount of Cl for the dicarbollide reaction plus the stoichiometric amount of Cl for converting the iron to ferric chloride would be sufficient. In practice, such good mixing is very difficult to obtain. The first solid obtained in Example 1 is washed with water to remove $FeCl_3$. The purpose of mixing the washed solid with a solvent and filtering is to remove iron and any unsoluble materials.

EXAMPLE 2

Trimethylammonium cobalt dicarbollide (0.40 g, 1.03 mmol) and N-bromosuccinimide (0.60 g, 3.37 mmol) were dissolved in 100 ml of THF, and the resulting dark brown clear solution was refluxed for 20 minutes. The solution was evaporated to dryness and washed with water to obtain 0.50 g of trimethyl ammonium cobalt dibromo dicarbollide, a dark orange solid. Yield:89%.

Trimethyl ammonium cobalt dibromo dicarbollide was made in a similar manner and it is believed that the diiodo compound can be made in a similar manner. Inventive compounds whose cations are tetramethylammonium, H, Li, Na, K, Rb, and Cs can be made in the same manner. Polar organic solvents which do not react with N-halosuccinimides may be used instead of THF. The reaction takes place slowly at room temperature. Increasing the temperature of the reaction solution decreases the time required for the reaction. It is necessary to use only a very slight excess of the N-halosuccinimide for complete dihalogenation and the reaction does not proceed to halogenation of boron atoms in addition to those in the number 10 positions even when large excesses of N-halosuccinimides are used.

It is believed that substituted cobalt dicarbollides can be halogenated in the same manner. The chemical literature may be consulted for methods of preparation of substituted cobalt dicarbollides. The term "substituted" refers to a cobalt dicarbollide anion having a group attached to one or more of the carbon and boron atoms of the two cobalt dicarbollide cages. There may be as many as 21 substituent groups; in this case, only one of the number 10 positions would be available for halogenation by use of N-halosuccinimide. The substituent groups which may be attached are limited to those having a particular linking atom which attaches to the carbon atoms and/or boron atoms of the cages, where the linking atom is one of a group consisting of carbon, oxygen, nitrogen, phosphorus, or sulfur. If all 22 of the primary cage atoms have a substituent group instead of a hydrogen atom attached, halogenation of the primary cage atoms will not take place. If both number 10 boron atoms have hydrogens and there are substituents at the other 20 positions, dihalogenation will take place. The reaction with N-halosuccinimide is sufficiently gentle so that the substituent groups will not be destroyed or substantially altered, though halogens may be added to the substituent groups. Halogenated x cobalt dicarbollide may be chemically attached to a substrate comprised of silicon oxides or aluminum oxides or to a polymer backbone by means of these substituent groups or by means of the halogens in the number 10 positions. The substituent groups may be organic or inorganic, but will always be attached to the cage carbons and/or borons through one of the five atoms mentioned above. Examples of substitutents are —$CH_3$, —COOH, —$C_2H_3$, —$CONH_2$, —SH, —$NH_2$, and —$OSO_2$. In future experimentation, it is planned to halogenate cobalt dicarbollide which is bound to an oxygen of a polysulfonamide through a cage carbon and cobalt dicarbollide attached to a nitrogen of a polyaniline. N-bromosuccinimide was reacted with $Cs[Co((CH_3)_2C_2B_9H_9)_2]$ and it is believed that it was dihalogenated, though characterization of the reaction product was not completed.

EXAMPLE 3

Tetramethylammonium cobalt dicarbollide (0.62 g, 1.36 mmol) was added to 20 ml of 6M HCl and then 50 ml of a solution of 10 wt % sodium hypochlorite (NaOCl) in water was added to the resulting mixture in dropwise fashion. The resulting yellow slurry was stirred for 24 hours at about 25° C. 50 ml of acetonitrile ($CH_3CN$) was mixed with the slurry and two layers were allowed to form. The resulting clear yellow organic layer was separated from the clear colorless aqueous layer and evaporated to dryness, yielding 0.62 g of tetramethyl ammonium cobalt dichloro dicarbollide. Yield:85%.

In other experimentation at 25° C., it was found that the reaction of Example 3 was 80% complete in two hours and 100% complete in six hours. A higher temperature will result in a shorter reaction time, but may also result in occurrence of side reactions. It can be seen in the above example that a large excess of the reagents were used; this was done because the reaction is heterogeneous. Use of HCl without NaOCl and NaOCl without HCl did not result in the dihalogenated compounds of this invention. The solution must be acidic; it is believed that a pH of about 6.0 or less is required and that a lower pH will have no further effect.

At this time, it is unclear whether forming a mixture of tetramethyl ammoniu cobalt dicarbollide, HCl, water, and NaOCl would be more or less desirable than the dropwise addition of the above example. Trimethyl ammonium cobalt dicarbollide and cesium cobalt dicarbollide could not be used as starting materials. The reason for this may be that their solubility permits intimate contact of dicarbollide with localized areas of high pH momentarily caused by addition of NaOCl solution, thus causing degradation of the dicarbollide before halogenation takes place.

Since tetramethyl ammonium cobalt dicarbollide is insoluble, it is possible that the reaction of cobalt dicarbollide was sufficiently slow to allow formation of HOCl from NaOCl and HCl before degradation took place.

It is believed that hypobromous acid and hypoiodus acid and any tetraalkylammonium cobalt dicarbollide, where the alkyl group has from one to eight carbon atoms, may be used in this reaction system. The hypohalous acid may be formed by reaction of various salts comprised of hypohalite anions, such as KOCl and strong acids. Hydrochloric acid, sulfuric acid, and nitric acid are preferred, but phosphoric acid and glacial acetic acid may be used. Hypochlorous acid may be formed by bubbling chlorine monoxide ($Cl_2O$) into a reaction mixture of tetraalkylammonium cobalt dicarbollide having a pH of about 6.0 or less. Polar organic solvents other than acetonitrile may be used for extraction of dihalogenated dicarbollide.

Tetramethylammonium cobalt dicarbollide and trimethylammonium cobalt dicarbollide were prepared by means of literature procedures except that n-propanol was substituted for ethanol in the preparation of the intermediate $[Me_3NH]$ $[C_2B_9H_{12}]$. By reference to such procedures, those skilled in the art can easily prepare the above compounds and cobalt dicarbollide compounds where the cations are hydrogen, lithium, sodium, potassium, rubidium, or cesium. These eight cations are easily substituted for one another in cobalt dicarbollide and dihalogenated cobalt dicarbollide compounds. A primary source for synthesis procedures is a paper by M. Hawthorne, D. Young, T. Andrews, D. Howe, R. Pilling, D. Pitts, M. Reintjes, L. Warren, and P. Wegner, *J. Am. Chem. Soc.* 90, 879–896 (1968). Additional sources are M. Hawthorne, *Accounts Chem.*, Res. 1, 281–288 (1968); M. Hawthorne and T. Andrews, *Chem. Commun.*, 443–444 (1965); and L. Warren and M. Hawthorne, *J. Am. Chem. Soc.*, 89, 470–471 (1967). The most advantageous synthesis involves three steps. First, orthocarborane ($1,2-C_2B_{10}H_{12}$) is degraded with alcoholic alkali metal hydroxide (NaOH or KOH in $CH_3OH$ or $C_2H_5OH$). It is believed that deprotonated alcohol anion abstracts a $BH^{2+}$ unit from the orthocarborane to briefly create the dicarbollide dianion $[C_2B_9H_{11}]^{2-}$ as an intermediate. However, the solution is only weakly basic, and $[C_2B_9H_{11}]^{2-}$ is protonated by solvent to give $[C_2B_9H_{12}]^-$. The overall result of this step is abstraction of B+ from orthocarborane. In the second step, dicarbollide anion is generated by treating $[C_2B_9H_{12}]^-$ with hot aqueous concentrated alkali metal hydroxide (40% by weight) to form $[C_2B_9H_{11}]^{2-}$. Finally, the $[C_2B_9H_{11}]^{2-}$ reacts in situ with cobalt(II) chloride ($CoCl_2$) to give cobalt (III) dicarbollide. The last step involves disproportionation by 1.5 equivalents of Co(II) to give one equivalent of Co(III) complex and 0.5 equivalents of Co(0) metal. The molecular weight of cobalt dicarbollide is 323.73 g/mol.

What is claimed is:

1. A process for halogenating cobalt dicarbollide anions in which a halogen atom is added only to a boron atom located in the number 10 position of each cage of a cobalt dicarbollide anion or substituted cobalt dicarbollide anion, said process comprising:

a. reacting cobalt dicarbollide anions with a halogenation agent selected from a group consisting of an N-halosuccinimide, hypohalous acid, and iron and gaseous chlorine, where the halogen of said hypohalous acid or N-halosuccinimide is chosen from a group consisting of chlorine, bromine, and iodine, and where said reaction is conducted by a method chosen from a group consisting of:

(1) forming a mixture comprised of tetraalkylammonium cobalt dicarbollide, hypohalous acid, and water and agitating said mixture for a time period sufficient for halogenation to take place, where the pH of said mixture is less than about 6.0;

(2) forming a mixture comprised of finely divided iron, a polar organic solvent, and x cobalt dicarbollide and adding chlorine gas to said mixture for a period of time sufficient for chlorination to take place, where the number of moles of iron in said mixture is equal to at least half the number of moles of x cobalt dicarbollide and where x is a cation chosen from a group consisting of hydrogen, lithium, sodium, potassium, rubidium, cesium, trialkylammoniium, and tetraalkylammonium; and (3) forming a solution of x cobalt dicarbollide or a substituted x cobalt dicarbollide and an N-halosuccinimide in a polar organic solvent and agitating the solution for a time period sufficient for halogenation to take place; where x is a cation chosen from a group consisting of hydrogen, lithium, sodium, potassium, rubidium. cesium, trialkylammoniium, and tetraalkylammonium, and where said substituted x cobalt dicarbollide has a substituent group attached to one or more of the carbon and boron atoms of the cobalt dicarbollide anion cages by means of a linking atom chosen from a group consisting of carbon, oxygen, nitrogen, phosphorus, or sulfur; and b. recovering from said mixture or solution a solid material comprised of cobalt dihalo dicarbollide or a substituted cobalt dihalo dicarbollide.

2. A process for chlorinating cobalt dicarbollide anions in which a chlorine atom is added only to a boron atom located in the number 10 position of each cage of a cobalt dicarbollide anion, said process comprising:

a. forming a mixture comprised of finely divided iron, a polar organic solvent, and x cobalt dicarbollide, where x is a cation chosen from a group consisting of hydrogen, lithium, sodium, potassium, rubidium, cesium, trialkylammonium, and tetraalkylammonium, where the alkyl groups of said cations contain from one to eight carbon atoms, and where the number of moles of iron in said mixture is equal to at least half the number of moles of x cobalt dicarbollide;

b. adding chlorine gas to said mixture for a period of time sufficient for chlorination to take place; and c. recovering x cobalt dichloro dicarbollide from the mixture.

3. The process of claim 2 where x cobalt dichloro dicarbollide is recovered by a method comprised of:

a. evaporating said mixture to dryness to form a solid;
b. washing said solid with water;
c. mixing the solid with a polar organic solvent and filtering the resulting mixture; and d. evaporating to dryness the resulting filtrate to isolate x cobalt dichloro dicarbollide.

4. A process for halogenating tetraalkylammonium cobalt dicarbollide in which a halogen atom is added only to a boron atom located in the number 10 position of each cage of a cobalt dicarbollide anion, said process comprising:

a. forming a mixture comprised of tetraalkylammonium cobalt dicarbollide, hypohalous acid, and water and agitating said mixture for a time period sufficient for halogenation to take place, where said hypohalous acid is chosen from a group consisting of hypochlorons acid, hypobromous acid, and hypoiodus acid, where the pH of said mixture is less than about 6.0, and where the alkyl groups of tetraalkylammonium cobalt dicarbollide contain from one to eight carbon atoms; and b. recovering tetraalkylammonium cobalt dihalo dicarbollide from said mixture.

5. The process of claim 4 where tetraalkylammonium cobalt dihalo dicarbolllide is recovered by a method comprised of:

a. mixing a polar organic solvent with said mixture and separating the resulting extraction mixture into an organic phase and an aqueous phase; and b. evaporating said organic phase to dryness to isolate tetraalkylammonium cobalt dihalo dicarbollide.

6. The process of claim 4 where said hypohalous acid is formed by reaction of a salt comprised of a hypohalite anion and an acid from a group consisting of hydrochloric acid, nitric acid, sulfuric acid, phosphoric acid, and acetic acid, where said hypohalite anion is chosen from a group consisting of hypochlorous, hypobromous, and hypoiodus.

7. The process of claim 4 where said hypohalous acid is formed by reaction of sodium hypochlorite and hydrogen chloride.

8. The process of claim 4 where said hypohalous acid is formed by reaction of chlorine monoxide and water.

9. A process for halogenating cobalt dicarbollide anions in which a halogen atom is added only to a boron atom located in the number 10 position of each cage of a cobalt dicarbollide anion or substituted cobalt dicarbollide anion, said process comprising:

a. forming a solution of x cobalt dicarbollide or a substituted x cobalt dicarbollide in a polar organic solvent, where x is a cation chosen from a group consisting of hydrogen, lithium, sodium, potassium, rubidium, cesium, trialkylammonium, and tetraalkylammonium, and where said substituted x cobalt dicarbollide has a substituent group attached to one or more of the carbon and boron atoms of the cobalt dicarbollide anion cages by means of a linking atom chosen from a group consisting of carbon, oxygen, nitrogen, phosphorus, or sulfur;

b. adding an N-halosuccinimide to said solution and agitating the solution for a time period sufficient for halogenation to take place, where said N-halosuccinimide is chosen from a group consisting of N-chlorosuccinimide, N-bromosuccinimide, and N-iodosuccinimide; and c. evaporating the solution to dryness to isolate x cobalt dihalo dicarbollide or a substituted x cobalt dihalo dicarbollide.

10. The process of claim 9 where said solution is heated to a temperature of from about room temperature to about the boiling point of the solution during said halogenation time period.

* * * * *